United States Patent
Kim et al.

(10) Patent No.: US 10,004,575 B2
(45) Date of Patent: Jun. 26, 2018

(54) DENTAL IMPLANT COATED WITH A MIXED SOLUTION OF CHEMICAL BUFFERING AGENT AND ORGANIC AMPHIPHILIC SUBSTANCE AND A PREPARATION PROCESS THEREOF

(71) Applicant: OSSTEMIMPLANT CO., LTD., Seoul (KR)

(72) Inventors: Su Kyoung Kim, Busan (KR); Il Seok Jang, Busan (KR); Ju Dong Song, Busan (KR); Tae Gwan Eom, Busan (KR); Kyoo Ok Choi, Seoul (KR)

(73) Assignee: OSSTEMIMPLANT CO., LTD, Seoul (KR)

( * ) Notice: Subject to any disclaimer, the term of this patent is extended or adjusted under 35 U.S.C. 154(b) by 106 days.

(21) Appl. No.: 14/786,407

(22) PCT Filed: Apr. 23, 2014

(86) PCT No.: PCT/KR2014/003550
§ 371 (c)(1),
(2) Date: Oct. 22, 2015

(87) PCT Pub. No.: WO2014/175657
PCT Pub. Date: Oct. 30, 2014

(65) Prior Publication Data
US 2016/0058528 A1    Mar. 3, 2016

(30) Foreign Application Priority Data

Apr. 24, 2013 (KR) .................. 10-2013-0045602

(51) Int. Cl.
*A61C 13/08* (2006.01)
*A61C 8/00* (2006.01)
(Continued)

(52) U.S. Cl.
CPC .......... *A61C 8/0015* (2013.01); *A61C 8/0013* (2013.01); *A61L 27/06* (2013.01);
(Continued)

(58) Field of Classification Search
CPC ..... A61C 8/0015; A61C 8/0013; A61L 27/06; A61L 27/14; A61L 27/28; A61L 2430/12
(Continued)

(56) References Cited

U.S. PATENT DOCUMENTS 6,702,855 B1    3/2004  Steinemann et al.
2013/0030361 A1   1/2013  Astrand et al.

FOREIGN PATENT DOCUMENTS

KR    10-2009-0042929 A    5/2009
KR       20090042929 A  *  5/2009  ........... A61C 8/0012
(Continued)

OTHER PUBLICATIONS

Search Report for International Application No. PCT/KR2014/003550.
(Continued)

*Primary Examiner* — Heidi M Eide
(74) *Attorney, Agent, or Firm* — LRK Patent Law Firm

(57) ABSTRACT

A bioactive-type of hydrophilic dental implant which is made of titanium or titanium alloy having a rough surface, wherein a coating layer of a mixed solution comprising i) an organic pH buffering agent and/or inorganic pH buffering agent and ii) an organic amphiphilic having sulfonic group is formed on the rough surface which was pre-treated to remove a contaminant. The present invention has effects preventing that the dental implant is exposed to air before it is inserted into the alveolar bone and the implant surface is re-contaminated; improving the biocompatibility of the implant, fluid- and blood-affinity, and the initial osseointegration performance; and shortening the osseointegration
(Continued)

period, and the surface of the dental implant can be maintained as being hydrophilic for at least 3 years by using a mixed solution of pH buffering agent and organic amphiphilic substance having sulfonic group as a surface coating solution.

3 Claims, 10 Drawing Sheets

(51) Int. Cl.
*A61L 27/06* (2006.01)
*A61L 27/28* (2006.01)
*A61L 27/14* (2006.01)

(52) U.S. Cl.
CPC ............... *A61L 27/14* (2013.01); *A61L 27/28* (2013.01); *A61L 2430/12* (2013.01)

(58) Field of Classification Search
USPC ..................................................... 433/201.1
See application file for complete search history.

(56) References Cited

FOREIGN PATENT DOCUMENTS

| KR | 10-2009-0117807 A | | 11/2009 | | |
|---|---|---|---|---|---|
| KR | 20090117807 A | * | 11/2009 | ............ | A61L 27/22 |
| KR | 10-2010-0085982 A | | 7/2010 | | |
| KR | 10-2013-0028508 A | | 3/2013 | | |
| KR | 20130028508 A | * | 3/2013 | ............ | A61C 8/0087 |
| KR | 20130030361 A | * | 3/2013 | | |
| KR | 10-1248785 B1 | | 4/2013 | | |
| KR | 101248785 B1 | * | 4/2013 | ............. | A61L 27/06 |

OTHER PUBLICATIONS

Paul Predecki et al., "Attachment of bone to threaded implants by ingrowth and mechanical interlocking", Journal of Biomedical Materials Research, vol. 6, pp. 401-412, 1972.
Daniel Buser et al., "Influence surface characreristics in bone integration titanium implants. A histomorphometric study in miniature pigs", Journal of Biomedical Materials Research, vol. 25, pp. 889-902, Jul. 1991.
Takeo Suzuki et al., "Nonvolatile buffer coating of titanium to prevent its biological aging and for drug delivery", Biomaterials, vol. 31, pp. 4818-4828, 2010.
Warren K. Ramp et al., "Medium pH modulates matrix, mineral, and energy metabolism in cultured chick bones and osteoblast-like cells", Bone Miner, vol. 24, pp. 59-73, 1994.
L.L. Hench et al., "Biomaterials: an interfacial approach", Academic Press, 1982.
Timothy R. Arnett, "Extracellular pH regulates bone cell function", The Journal of Nutrition, vol. 138, pp. 415S-418S, 2008.
David H. Kohn et al., "Effects of pH on human bone marrow stromal cells in vitro: implications for tissue engineering of bone", Journal of Biomedical Materials Research, vol. 60, pp. 292-299, 2002.
A. Brandao-Burch et al., "Acidosis inhibits bone formation by osteoblasts in vitro by preventing mineralization", Calcified Tissue International, vol. 77, pp. 167-174, 2005.

* cited by examiner

DENTAL IMPLANT COATED WITH A MIXED SOLUTION OF CHEMICAL BUFFERING AGENT AND ORGANIC AMPHIPHILIC SUBSTANCE AND A PREPARATION PROCESS THEREOF

BACKGROUND OF THE INVENTION

1. Field of the Invention

The present invention relates to a dental implant coated with a mixed solution of organic or inorganic pH buffering agent (pH buffering substance) and organic amphiphilic substance, in order to improve a conventional RBM (Resorbable Blasted Media blasting) and SLA (Sandblast Large grit Acid etch) surface treatment manner which a implant surface of titanium or titanium alloy having a rough surface is contaminated with an organic contaminating source and to maintain the super-hydrophilicity of said implant surface for a long time, and a preparation process thereof. Through the present invention, a dental metal implant can be provided, wherein a bioactivity of RBM or SLA surface is improved, a fluid- and blood-affinity are improved and finally an excellent biocompatibility after an implant surgery, bone-forming effect and bioactivity having a short osseointegration period are enhanced.

2. Description of Related Art

The surface treatment of a dental implant has been recognized as an important factor in osseointegration, and a smooth surface-treatment method via a turning can be examplified as an implant surface-treatment method. Since the biocompatibility with a bone and tissue stability via such surface treatment can be enhanced, this treatment has been used in the implant surgery for a long time. In order to improve the success rate in the bone having a low bone-density, an effort to improve the surface property has been made, and since the implant having an irregular surface can have a fast bone growth and excellent mechanical adhesive force, it is suggested that the implant having an irregular and rough surface has higher bone contacting rate than the implant having a smooth surface. Upon reviewing the developing step of the implant surface, it can be divided into the first-generation implant having a smooth surface, the second-generation implant having a rough surface, and the third-generation implant having a chemically modified coating surface. Examples of the second-generation implant include RBM (Resorbable Blasted Media blasting), Titanium Plasma Spray (TPS), and the like. Also, the surface of the third-generation implant having hydroxyapatite (HA) coating surface has an advantage that the the surface area is increased due to the effect of the particle and coating being injected on the surface, the interface bone-binding force of the implant is increased and the the reaction of the cell is activated on the rough surface. However, in the case of said RBM or SLA, etc. which are the surface-treatment manner being currently, widely used, there are problems that an oxidation layer is growed when a product is exposed to air after the surface-treatment process, and the adsorption of various contaminating source such as hydrocarbon, etc. is proceeded to change into a chemically stable state while being hydrophobic. The resulting surface being hydrophobic has a low wettability to the fluid and blood, and therefore, there are disadvantages that the overall treatment or implanting procedure fusing with the bone after inserting the implant is interfered and the period that the implant is stabilized is extended.

According to U.S. Pat. No. 6,702,855 which is a prior art, in order to improve the hydrophocizing of the titanium implant surface, a method chemically oxidizing by using an inorganic acid such as hydrochloric acid, sulfuric acid, nitric acid, etc. is suggested, and a plasma treatment (Radio-Frequency Glow Diskharge; RFGD, $O_2$, etc.), light irradiation (ultraviolet ray, ultraviolet-ozone, etc.), and the like, can be considered as the method for imparting a hydrophobicity on other conventional known metal surface. Although it is possible that the titanium surface is super-hydrophilized during a short period, there is still a disadvantage in maintaining said ultrahydrophilicity for a long period; and although Suzuki, etc. suggests an example for hydrophilizing titanium surface by using 4-(2-Hydroxylethyl)-1-piperazineethanesulfonic acid, it is mere the degree that the hydrophilicity is maintained for only 3 months.

The hydrophilicizing of such dental implant surface belongs to very important factor in the initial bone-forming ability and biocompatibility of oral cell, wherein pH of the implant surface has also an important role in maintaining the hydrophilicity and surface property. In particular, it is well-known that the extra-cell, micro-environments such as a blood flow, nutrients, pH change, etc. make an effect on the activity of cell, morphological change and effect in various cell constituting a alveola bone including osteoblast, osteoclast, and the like (Ramp W K., Lenz L G. & Kaysinger K K.).

That is, it is well-known that the pH change due to the pathological environment including a biometabolic procedure, fracture, metabolic disease, or the implant of the biomaterial such as an implant, and the like, makes an effect on the proliferation and differentiation potency of the osteoblast and osteoclast existing at the periphery of the bone, and said extra-cell pH change in the body is now strictly controlled in order to maintain the acid-base equilibrium of the body. However, it is known that these equilibrium induces acidosis or alkalosis by breaking the acid-base equilibrium for several reasons, and typically it is known that the pH of the intra-bone micro-environment is rapidly decreased in the pathological environment such as a fracture, etc., or a surgical treatment such as a drilling (surgical action making a hole in a similar shape so as to implant the implant fixture in the alveolar bone) or bone deletion which is performed to make the aveloar bone smooth in implanting the plant, and the state of about pH 4~5 is maintained for 1~2 weeks (Hench L L. & Ethridge E C.).

In the study relating to bone-metabolism according to pH change, it is known that if an acidification is occurred when pH is lowered, the activity of oestoblast is decreased and a collagen accumulation of extracellular matrix (ECM) is inhibited and alkaline phosphatase (ALP) activity and gene expression as well as the expression of osterix and Runx2 which are major transfetation factor related to the bone forming are decreased and thus, the mineralization of bone is inhibited and retarded, and the pH lowering activates the osteoclast by increasing the expression of receptor activator of nuclear factor kappa-B ligand (RANKL) and parathyroid hormone receptor, and may cause even bone loss by promoting the bone remodeling, in view of long period.

Meanwhile, it is reported that if pH is increased to be an alkaline, the activity of osteoblast is increased unlike the acidification, and ALP activity and collagen synthesis are increased, and the differentiation of bone marrow stromal cell into osteoblast is also increased. Through this, the mineralization of ECM in the bone environment is promoted, and the positive phenomenon that the bone formation is increased is occurred (Arnett T R., Kohn et al., Brandao-Burch A. et al.).

Like this, upon synthesizing conventional technical references of the prior art that the pH of micro-environment within the bone affects on the bone formation, the matter making that the pH of the inserting part of the implant is uniformly maintained from neutral to weak-alkaline is important since it affects on the implant success rate in view of the long period as well as the bone formation of implant-bone interface.

Therefore, the present invention is to provide the dental implant wherein the matter that the implant surface is re-contaminated to the organic contamination source to change into a hydrophobic, is inhibited by using a mixed solution comprising an alkaline pH buffering agent and organic amphiphilic substance (in particular, organic amphiphilic substance having a sulfonic group), implant biocompatibility and, fluid- and blood-affinity, initial osseointegration performance are enhanced, and the osseointegration period is shortened, so that the initial bone-forming ability and biocompatibility are able to be improved by neutralizing the initial pH of the inserting part of the dental implant and maintaining the resulting properly controlled micro-environment.

SUMMARY OF THE INVENTION

The present invention is a technique to improve a fluid- and blood-affinity and finally to have an excellent bone-forming effect and short osseointegration period after an implant surgery, by uniformly coating a mixed solution comprising a pH buffering agent on a titanium surface; inhibiting re-adsorption and stabilization of contaminant which causes a hydrophobizing of the surface; maintaining a super-hydrophilicity of titanium surface.

In order to achieve the above, said technique comprises 1) the step of exposing a super-hydrophilic titanium surface having bioactivity by adsorbing it on the titanium oxidation film and removing stabilized contaminant; 2) forming a uniform coating film by coating a mixed solution comprising an organic amphiphilic substance having a sulfonic group.

As can be seen from FIG. 1, on the bioactivation surface-treated metal implant prepared by the method of the metal implant a film is formed which is uniformly coated with the mixed solution comprising the organic amphiphilic substance having sulfonic group and pH buffering agent after removing the contaminant of the implant surface.

As the dental implant made of a titanium or titanium ally having rough surface, it has characteristics improving the hydrophilicity of the surface and osseointegration performance by improving hydroxylation of the surface of the dental implant, by coating the mixed solution comprising the organic amphiphilic substance having sulfonic group. In particular, it can impart an effect to maintain the improved hydrophilicity and osseointegration performance of the dental implant for a long time without any reduction.

It is preferable that said amphiphilic substance having sulfonic group comprised in said mixed solution has a concentration in the range of 0.05~1.68M, and said pH buffering agent can be used in the range of 1~10 wt % of said mixed solution.

In addition, it is preferable that said mixed solution is uniformly coated on the implant surface by using about 20 μl of it, and finally it is preferable that the mixed solution of the pH buffering agent and the organic amphiphilic substance is coated on the implant surface in the range of 0.02~0.05 μl/mm².

The said organic amphiphilic substance having sulfonic group comprised in said mixed solution may include at least one of ACES (2-(carbamoylmethylamino)ethane sulfonic acid), BES (N,N-bis(2-hydroxyl-2-amino)ethane sulfonic acid), CHES ((cyclohexylamino)ethane sulfonic acid), HEPES (4-(2-hydroxyethyl)-1-piperazine sulfonic acid), MOPS (3-(N-morpholino)propane sulfonic acid), PIPES (1,4-piperazine diethane sulfonic acid) and TES (N-tris (hydroxymethyl)methyl)-2-aminoethane sulfonic acid).

The said inorganic pH buffering agent acts as a base having hydroxyl group, and may be selected from at least one or more of NaOH, KOH, $Ca(OH)_2$, $Ba(OH)_2$, $Al(OH)_3$ and $Sr(OH)_2$. Also, said pH buffering agent acts as a base having pH of 8 or more, and the pKa value of it is 8.0 or more, and specifically at least one or more of AMPD(2-amino-2-methyl-1,3-propanediol), ammonia, bicine, glycine, glycylglycine, tris, tricine and taurine can be used.

A method for preparing the bioactive hydrophilic dental implant which is another embodiment of the present invention, comprising the first step of preparing the dental implant made of titanium or titanium alloy; the second step of roughening the surface of the dental implant; the third step of removing the contaminant by pre-treating the surface of the dental implant being roughly treated; and the fourth step of forming the coating layer of the mixed solution comprising the organic pH buffering agent and/or inorganic pH buffering agent and the organic amphiphilic substance having sulfonic group, wherein the said organic pH buffering agent has 8.0 or more of pKa, and is at least one or more selected from AMPD, ammonia, bicine, glycine, glycylglycine, tris, tricine and taurine; the said inorganic pH buffering agent is characterized in that it has hydroxyl group and is at least one or more selected from NaOH, KOH, $Ca(OH)_2$, $Ba(OH)_2$, $Al(OH)_3$ and $Sr(OH)_2$.

At this time, the step of removing the contaminant may include the treatment of the roughly treated surface of the dental implant with at least one or more of the ultraviolet ray, RFGD (radio-frequency glow discharge), oxygen and room temperature plasma, and the pre-treatment step can be omitted depending on the circumstance.

According to the metal implant and the method for preparing the same according to the present invention, the present invention has effects which the biocompatibility of the implant, fluid- and blood-affinity, and initial osseointegration performance can be improved, by avoiding that the implant surface is re-contaminated by the organic contaminant since the dental implant is exposed to air before implanting to the alveolar bone, and is changed into hydrophobic because of the re-contaminating by avoiding the bioactivity-lowering due to the surface-hydrophobizing, by surface-coating the dental implant which the organic contaminant of the surface is removed through the pre-treatment such as plasma or light-irradiation, etc. with the mixed solution comprising the organic amphiphilic substance (BES, HEPES, MOPS, PIPES, TES) having sulfonic group and the pH buffering agent.

In addition, since the organic pH buffering agent and organic amphiphilic substance are coated on the implant surface, the coating layer being uniformly formed on the surface represents the biocompatibility and fluid- and blood-affinity as well as that the adsorption of the contaminant in the air of the surface is effectively avoided. Therefore, there are effects that the initial osseointegration performance after the implant surgery is improved, and finally the osseointegration period is shortened.

There are effects that the bone-forming of the implant-bone interface and also the success rate of the implanting in view of long period can be improved, and the dental implant surface can be maintained as the hydrophilicity for at least 3 years (which is the period corresponding to 18 weeks of the acceleration aging).

DETAILED DESCRIPTION OF THE INVENTION

Figure 1:
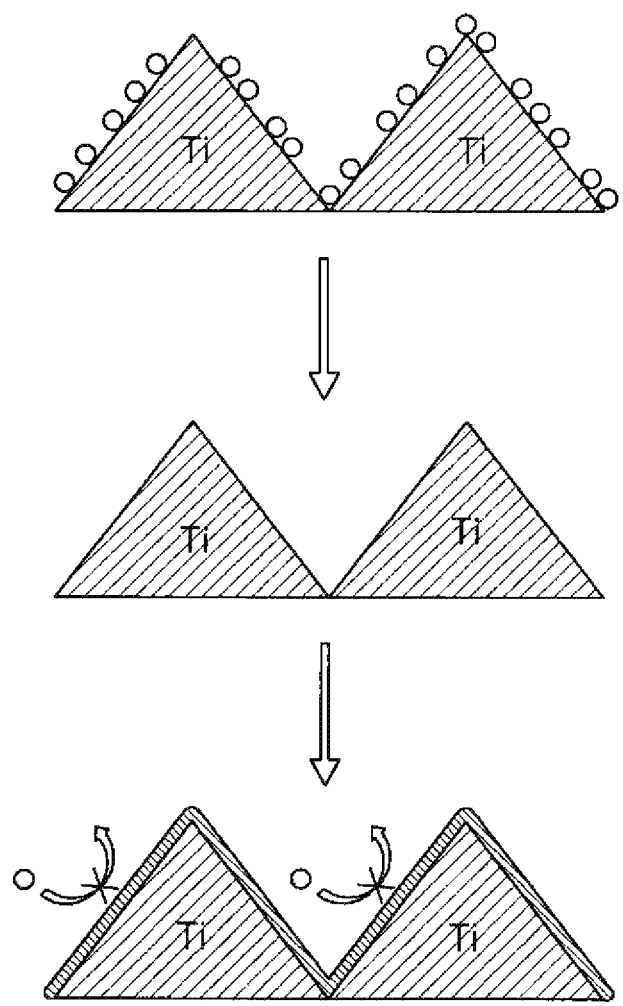
FIG. 1 schematically shows the method of preparing the metal implant of the present invention according to every step.

Hereinafter, an explanation on a functional implant according to the present invention will be described in detail with reference to the attached drawings. Prior to this, any terms or words used in the specification and claims of the present invention should not be construed as the conventional or dictionary meaning, and should be construed as the meaning and concept corresponding to the technical scope of the present invention based on that the inventors can define the concept of the term in order to illustrate their invention with the best ways.

Accordingly, the constitutions illustrated in the drawings and examples described in the specification of the present invention is no more than one most preferable example, and does not represent all the technical scope of the present invention, and thus, it should be understood that various equivalents and variation examples which can replace them can be present.

Example 1: Coating of pH Buffering Agent and Organic Amphiphilic Substance (1M)

Machined titanium implant is blasted by using 1 mm or less of $Al_2O_3$ powder for 1~60 sec with a blast pressure of 1~10 atmosphere, and then a micro-morphology can be formed on the implant surface by using an acid treating method using the aqueous solution of the mixed acids. The dental titanium implant thus acid-treated is subjected to the drying step after microwave-washing it with ethanol and distilled water for 30 min, respectively.

A plasma-treatment for 1 min or an ultraviolet light-treatment for 5 min were subjected to the implant surface subjected to the drying step to remove the adsorbed and stabilized contaminant on the surface was removed, and 1M of aqueous solution of the organic amphiphilic substance (BES, HEPES, TES) having pH buffering agent and not having sulfonic group was uniformly coated on said implant surface (see FIG. 1), in an amount of 10 μl and the mixed solution of said organic amphiphilic substance and pH buffering agent was coated on the implant surface in the range of 0.02~0.5 μl/mm².

When said pH buffering agent is used, the mixed solution of the organic amphiphilic substance and pH buffering agent was used in coating the implant surface. At this time, the inorganic pH buffering agent such as NaOH, KOH, Ca(OH)$_2$, Ba(OH)$_2$, Al(OH)$_3$ and Sr(OH)$_2$, and the like, was used as the pH buffering agent in the range of 1~10 wt %, and instead of said inorganic pH buffering agent, at least one or more selected from AMPD, ammonia, bicine, glycine, glycylglycine, tris, tricine and taurine can be used in the range of 0.01~1.68M of the total mixed solution. Also, the mixture of said inorganic pH buffering agent and said organic pH buffering agent can be used in said mixed solution together with the organic amphiphilic substance having sulfonic group, and in the following examples NaOH which is an inorganic pH buffering agent was used.

The implant which includes or does not include the pH buffering agent thus prepared was used in Example 2 as below.

Example 2: Measurement of Bone-Interface Binding Force of the Dental Implant Depending on the Presence or Absence of pH Buffering Agent A bone-interface binding force of the coated dental implant was measured under the acceleration aging (hereinafter, referred to as 'AA') for the case that the solution comprising the organic amphiphilic substance (BES, HEPES, TES) contains the pH buffering substance and the case that said solution does not contain said buffering agent. BES, HEPES, TES coating-dental implants prepared in said Example 1 were left for 18 weeks (corresponding to 3 years of the conventional storing period, acceleration aging 18 weeks; hereinafter, referred to as 'AA18W' and defined like this) under the acceleration aging condition (about 55° C.), and then said implant is inserted to the lower jaw of a micropig in order to ascertain the implant-bone interface binding force, and after the bone-forming period of 16 days a removal torque was measured. At this time, the implant not removing the contaminant (SA) was used as the negative control, and the implant subjected to the Pre-treatment (hereinafter, referred to as 'PT') removing the contaminant was used as the positive control, and the bone-interface binding forces depending on the presence or absence of the pH buffering agent (hereinafter, referred to as 'BA') were compared.

Figure 2:
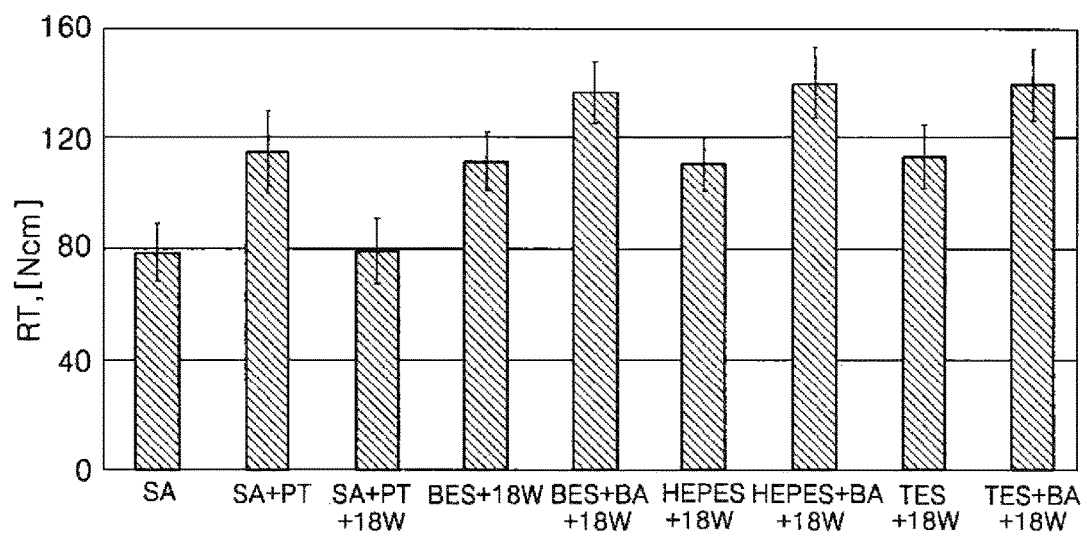
FIG. 2 shows the measurement results of the bone interface binding capability of the dental implant by dividing the case that the pH buffering agent (BA) is used and the case that said agent is not used in the mixed solution comprising the organic amphiphilic substance (BES, HEPES, TES) having sulfonic group and the pH buffering agent.

As seen from FIG. 2, the removal torque was increased to about 46% in the positive control (SA+PT) compared to the negative control (SA). Although the pre-treatment (PT) was made like the positive control (SA+PT), since the bioactivity and hydrophilicity were not maintained for the experiment group subjected to the acceleration aging (AA) of 18 weeks (18 W) corresponding to the storing period of 3 years, and thus, the removal torque was reduced in the level of the negative control, but for the BES, HEPES, TES coating experimental group the removal torque was maintained in the significant level compared to the positive control and in the level of about 42%, 41% and 44%, compared to the negative control.

Further, for BES, HEPES, TES-coating experimental group (with BA) wherein the pH buffering agent is contained, a significant synergic effect was confirmed that about 22%, 27%, 24% or more of the bone-interface binding force is additionally improved.

Example 3: Coating of Titanium Disk Surface by Using a Mixed Solution of the Organic Amphiphilic Substance Having Sulfonic Group and the pH Buffering Agent After removing the contaminant for the titanium disk surface, a coating layer was formed by using a mixed solution of the pH buffering agent and the organic amphiphilic substance having sulfonic group. The machined titanium disk was blasted for 1~60 see at the pressure of 1~10 atmosphere by using 1 mm or less of $Al_2O_3$ powder, and then a macro- and micro-morphology was formed on the implant surface via acid-treatment method by using an aqueous solution of mixed acids. Said dental titanium disk which was subjected to the acid-etching treatment was ultrasonic-washed by using ethanol and distilled water for 30 min, respectively, and then dried.

The rough disk via said drying step was subjected to the plasma treatment for 1 min or the ultraviolet-light treatment for 5 min to remove the adsorbed and stabilized contaminant, and 10 µl of the mixed solution of the organic amphiphilic material (ACES, BES, CHES, HEPES, MOPS, PIPES, TES, etc.) having sulfonic group in a concentration of 1M and the pH buffering agent was uniformly coated on said surface to manufacture the disk. The titanium disk that the mixed solution of the organic amphiphilic substance and the pH buffering agent thus prepared was used in the following Examples 4 and 5.

Example 4: Measurement of Contact Angle after Acceleration Aging-Treatment of the Coated Titanium Disk After the titanium disk wherein the mixed solution of the pH buffering agent and the organic amphiphilic substance having sulfonic group was subjected to the acceleration aging-treatment, the contact angle was measured.

The titanium disk manufactured from said Example 3 was left under the acceleration aging condition (about 55° C.) for 2 weeks (2 W), 4 weeks (4 W), 6 weeks (6 W) and 12 weeks (12 W), and then 5 ml of distilled water was dropped on said disk, and the contact angle was measured by near-photographing it at the side. At this time, although the implant which the contaminant was not removed (SA) was used as the negative control, the titanium disk which the pre-treatment procedure to remove the contaminant was subjected but said mixed solution is not coated (SA+PT) was used as the positive control.

Figure 3:
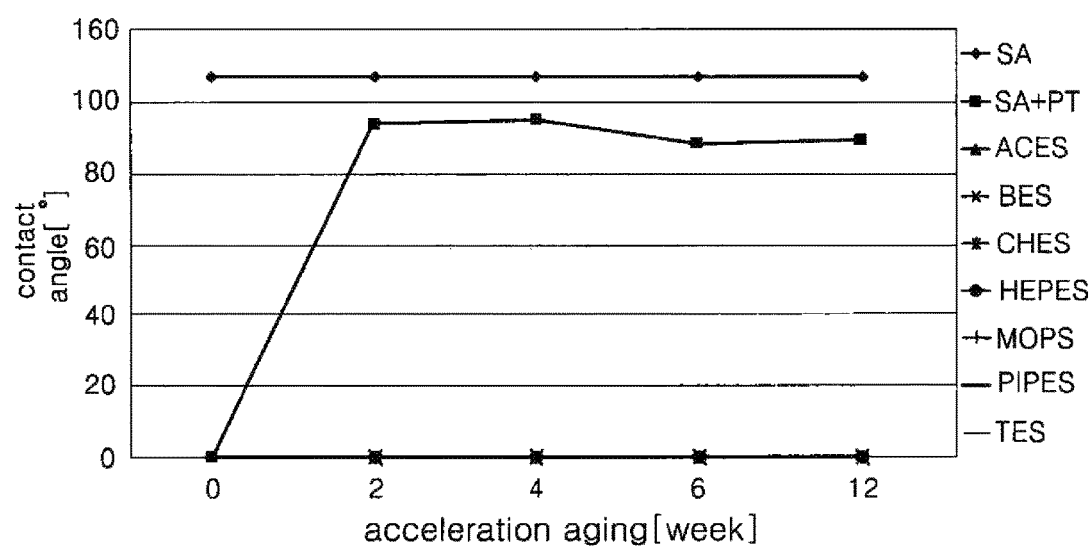
FIG. 3 shows the test results of the contact angle of the titanium disk coated with the mixed solution comprising the organic amphiphilic substance (ACES, BES, CHES, HEPES, MOPS, PIPES, TES) having sulfonic group and the pH buffering agent.

As can be seen from the result of FIG. 3, the contact angle of the negative control was 107°, and that of the positive control and experimental control was 0°, and also if the acceleration aging is subjected, the contact angle of the positive control is increased, and thus the super-hydrophilicity was not maintained, whereas the titanium disk that the mixed solution of the organic amphiphilic material having pH buffering agent and the organic amphiphilic material having sulfonic group maintained the contact angel of 0° even through the acceleration aging, and thus it was confirmed that the super-hydrophilicity was continuously maintained.

Example 5: Experiment of Cell-Adhering Capability after the Acceleration Aging of the Coated Titanium Disk A cell-adhering capability of the titanium disk wherein the mixed solution of the pH buffering agent and the organic amphiphilic substance having sulfonic group was coated, was measured.

After the titanium disk manufactured from said Example 3 was left for 2 weeks at the acceleration condition (about 55° C.), MG63 being osteoblast cell line was seeding with $1 \times 10^5$ cells/disk to measure the cell-adhering capability, and then culturing it for 1 hour to quantify the cell adhered on the disk surface with cresyl violet assay. At this time, the implant which the contaminant was not removed (SA+2 W) was used as the negative control, the implant which the pre-treatment procedure to remove the contaminant was subjected but said mixed solution is not coated (SA+PT) was used as the positive control.

Figure 4:
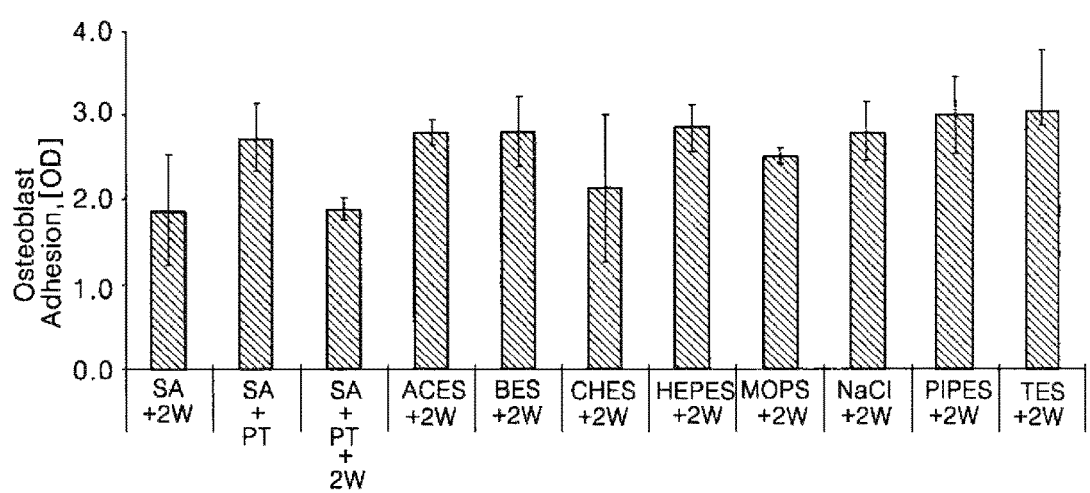
FIG. 4 shows the test results of the cell-adhering capability of the titanium disk left for 2 weeks (2 W) under the acceleration aging (AA) condition after coating with the mixed solution comprising the organic amphiphilic substance (ACES, BES, CHES, HEPES, MOPS, PIPES, TES) having sulfonic group and the pH buffering agent.

As can be seen from the results of FIG. 4, it can be confirmed that the cell adhesion was increased in the positive control compared to the negative control, and the cell adhesion was occurred in most of the experimental group in the level similar to the positive control (SA+PT), but after a lapse of the time of 2 weeks, the cell adhering performance of the positive control (SA+PT+2 W) was also decreased in the level similar to that of the negative control (SA+2 W). However, it could be confirmed that in the case of coating the organic substance of the present invention the cell adhering capability was maintained in a relatively high level even after a lapse of the time of 2 weeks. In particular, it could be confirmed that the cell adhesion was the most excellent in the titanium disk (TES+2 W) by using TES as the organic amphiphilic substance having sulfonic group.

Example 6: Coating of the Dental Implant Surface by Using a Mixed Solution (0.2M) of the pH Buffering Agent and the Organic Amphiphilic Substance Having Sulfonic Group The dental implant surface was coated on the surface of the dental implant by using the mixed solution of the pH buffering agent and the organic amphiphilic substance having sulfonic group. The machined titanium disk was blasted by using 1 mm or less of $Al_2O_3$ powder for 1~60 sec at the blast pressure of 1~10 atmosphere, and then a macro- and micro-morphology was formed on the implant surface via acid-treatment method by using an aqueous solution of mixed acids. Said dental titanium disk which was subjected to the acid-etching treatment was ultrasonic-washed by using ethanol and distilled water for 30 min, respectively, and then dried.

The rough disk via said drying step was subjected to the plasma treatment for 1 min or the ultraviolet-light treatment for 5 min to remove the adsorbed and stabilized contaminant, and 0.2M of the aqueous mixed solution of the organic amphiphilic material (BES, HEPES, MOPS, TES) having sulfonic group in a concentration of 1M and the pH buffering agent was uniformly coated in an amount of 10 µl on said surface of the implant to manufacture the disk. The titanium disk that the mixed solution of the organic amphiphilic substance and the pH buffering agent thus prepared was used in the following Examples 7 and 8.

Example 7: Measurement of Blood-Affinity and Blood-Protein Adhering Capability after the Acceleration Aging Treatment of the Dental Implant on which the Mixed Solution of the pH Buffering Agent and the Organic Amphiphilic Substance is Coated After the acceleration aging proceeded for the dental implant on which the mixed solution of the pH buffering agent and the organic amphiphilic substance is coated, the blood-affinity and blood-protein adhering capability was measured.

The dental implant manufactured by the method given in said Example 6 was left under the acceleration aging condition (about 75° C.) for 1.5 weeks (1.5 W), 3 weeks (3 W), 4.5 weeks (4.5 W) and 7.5 weeks (7.5 W), and then said implant was immersed in 5% BSA (bovine serum albumin) aqueous solution in a depth of about 1 mm to ascertain the adhering amount of the blood-protein, and BSA adhered on the surface was confirmed by BCA assay. At this time, the implant which the contaminant was not removed (SA) was used as the negative control, and the implant which the pre-treatment procedure to remove the contaminant was subjected but said mixed solution is not coated (SA+PT) was used as the positive control.

Figure 5:
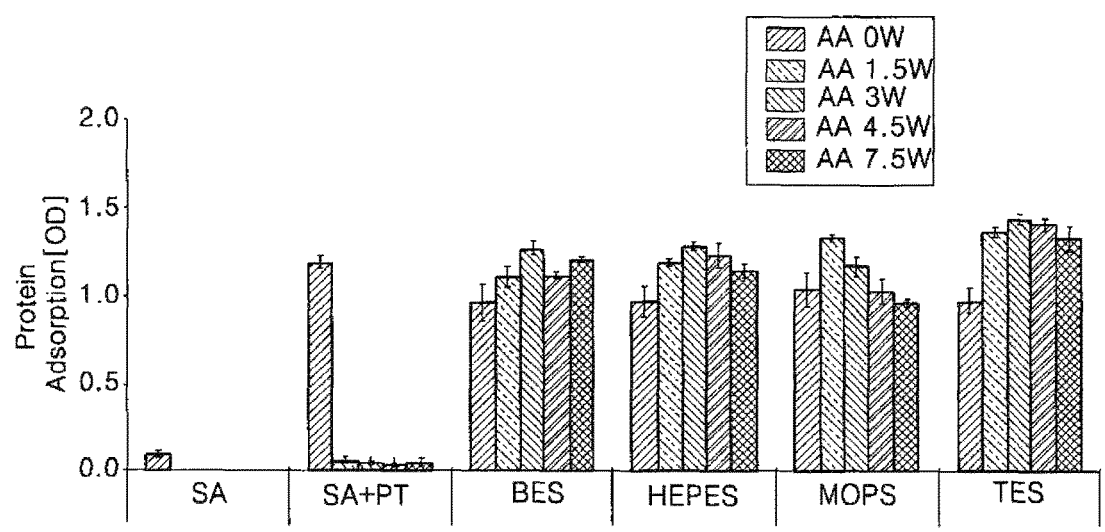
FIG. 5 shows the test results of the cell-adhering capability of the titanium disk left for various times (0 W, 1.5 W, 3 W, 4.5 W, 7.5 W) under the acceleration aging (AA) condition after coating with the mixed solution comprising the organic amphiphilic substance (BES, HEPES, MOPS, TES) having sulfonic group and the pH buffering agent.

As can be seen from the results of FIG. 5, it could be confirmed that despite the acceleration aging during 7.5 weeks (7.5 W), the adhering capability of the blood-protein of the implant on which the mixed solution of the pH buffering agent and the organic amphiphilic substance having sulfonic group is coated was maintained or increased. In particular, the adhering capability of the blood-protein was most excellent in the implant wherein TES is coated.

After leaving the dental implant on which the mixed solution of the pH buffering agent and the organic amphiphilic substance having sulfonic group is coated under the acceleration aging condition (about 75° C.) for 1.5 weeks (1.5 W) and 3 weeks (3 W), the said coated implant was immersed in a depth of 3 mm into the blood of the micropig to ascertain the blood-affinity, and then the blood-wettability of the blood was ascertained by the height of the blood coming up along the implant surface. At this time, as the control the implant which was subjected to the pre-treatment removing the contaminant but said material was not coated was used.

Figure 6:
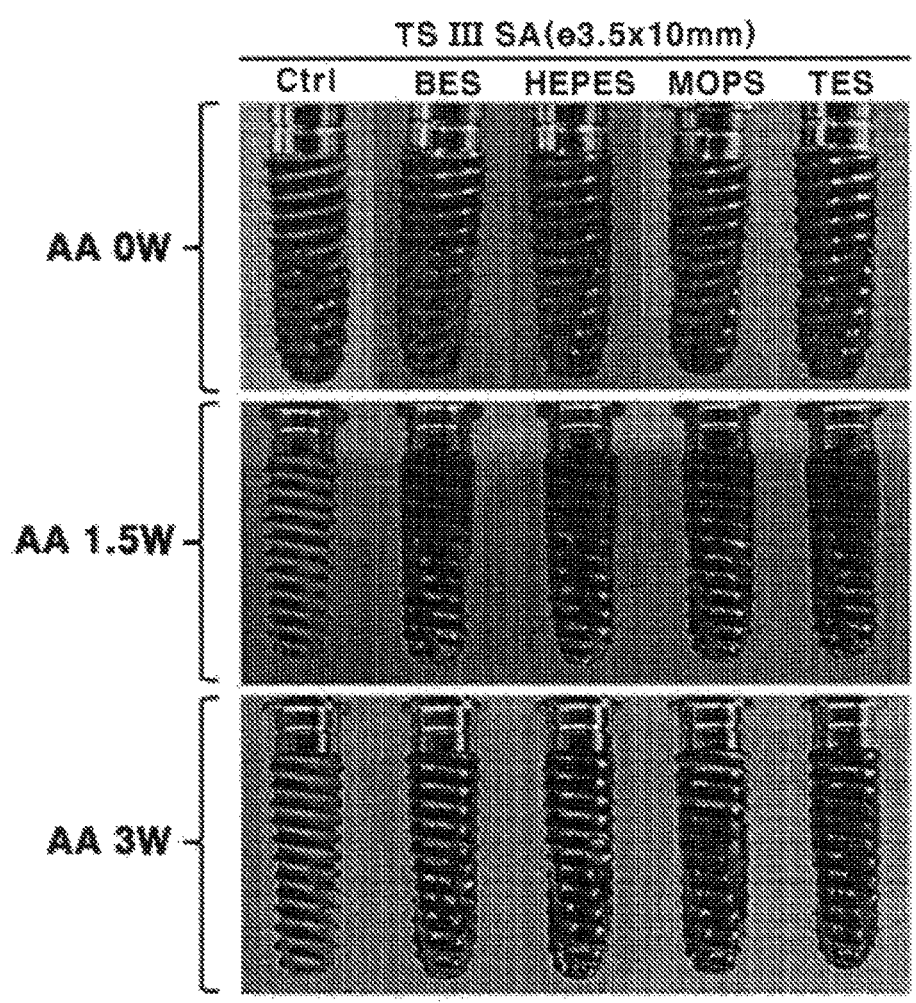
FIG. 6 shows the results representing the blood-wettability of the dental implant left for various times (0 W, 1.5 W, 3 W) under the acceleration aging (AA) condition after coating with the mixed solution comprising the organic amphiphilic substance (BES, HEPES, MOPS, TES) having sulfonic group and the pH buffering agent.

As can be seen from the photograph of FIG. 6, it could be visually ascertained that the implant on which the mixed solution of the pH buffering agent and the organic amphiphilic substance having sulfonic group has an excellent blood-wettability compared to that of the control implant, and the implant thus coated has much more blood-affinity. In particular, the blood-affinity was remarkably increased in the experimental group compared to the control as the time for acceleration aging is increased.

Example 8: Measurement of the Bone-Interface Binding Force after the Acceleration Aging Treatment of the Dental Implant on which the Mixed Solution is Coated After the acceleration aging of the dental implant on which the mixed solution of the pH buffering agent and the organic amphiphilic substance having sulfonic group is coated, the bone-interface binding force was measured. After leaving the dental implant on which the mixed solution prepared from said Example 6 under the acceleration aging condition (about 55° C.) for 2 weeks, the said implant was inserted into the lower jaw of the micropig to confirm the implant-bone interface binding force, and the removal torque was measured after the bone-forming period of 16 days. At this time, the implant which the contaminant was not removed was used as the negative control, and the implant which the pre-treatment procedure to remove the contaminant was subjected but said mixed solution is not coated was used as the positive control.

Figure 7:
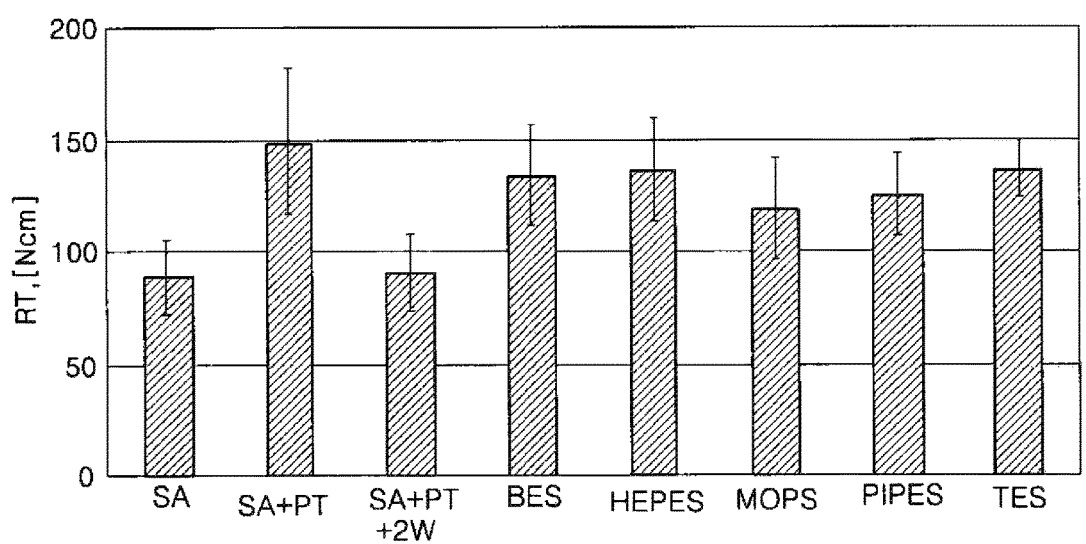
FIG. 7 shows the measurement results of the bone-binding capability treated with the acceleration aging (AA) condition after coating with the mixed solution comprising the organic amphiphilic substance (BES, HEPES, MOPS, PIPES, TES) having sulfonic group and the pH buffering agent.

As can be seen from FIG. 7, it was ascertained that the removal torque in the positive control (SA+PT) was increased to about 50% compared to that of the negative control (SA), and the removal torque of the experimental group was also increased to about 20~40% compared to the negative group. This improvement of the removal torque means that the implant-bone binding force is strengthened, and it could be seen that in all the experimental groups the improvement of the bone-interface binding force was maintained in the level which is in somewhat lower but similar level compared to that of the positive control.

Example 9: Coating of the Dental Implant Surface by Using the Mixed Solution (0.05~1.68M) of the pH Buffering Agent and the Organic Amphiphilic Substance Having Sulfonic Group The implant surface was coated by using the mixed solution of the pH buffering agent and the organic amphiphilic substance having sulfonic group.

The machined titanium disk was blasted for 1~60 sec at the blast pressure of 1~10 atmosphere by using 1 mm or less of $Al_2O_3$ powder, and then a macro- and micro-morphology was formed on the implant surface via an acid-treatment method by using an aqueous solution of mixed acids. Said dental titanium disk which was subjected to the acid-etching treatment was ultrasonic-washed by using ethanol and distilled water for 30 min, respectively, and then dried.

The rough disk via said drying step was subjected to the plasma treatment for 1 min or the ultraviolet-light treatment for 5 min to remove the adsorbed and stabilized contaminant (PT), and 10 μl of the aqueous solution of the organic amphiphilic material (BES, HEPES, TES) having sulfonic group in a concentration of 0.05~1.68M and pH buffering agent was uniformly coated on said surface. And, the dental implant thus prepared on which the mixed solution of the organic amphiphilic substance having sulfonic group and the pH buffering agent is coated was used in the following Example 10.

Example 10: Measurement of Blood-Protein Adhering Capability after the Acceleration Aging Treatment of the Dental Implant Coated with the Mixed Solution After the acceleration aging proceeded for the dental implant on which the mixed solution of the pH buffering agent and the organic amphiphilic substance having sulfonic group is coated, the adhering capability of the blood-protein was measured. The dental implant manufactured by the method given in said Example 9 was left under the acceleration aging condition (about 75° C.) for 6 weeks, and then said implant was immersed in 5% BSA (bovine serum albumin) aqueous solution in a depth of about 1 mm to ascertain the amount of the blood-protein, and BSA adhered on the surface was confirmed by BCA assay.

Figure 8:
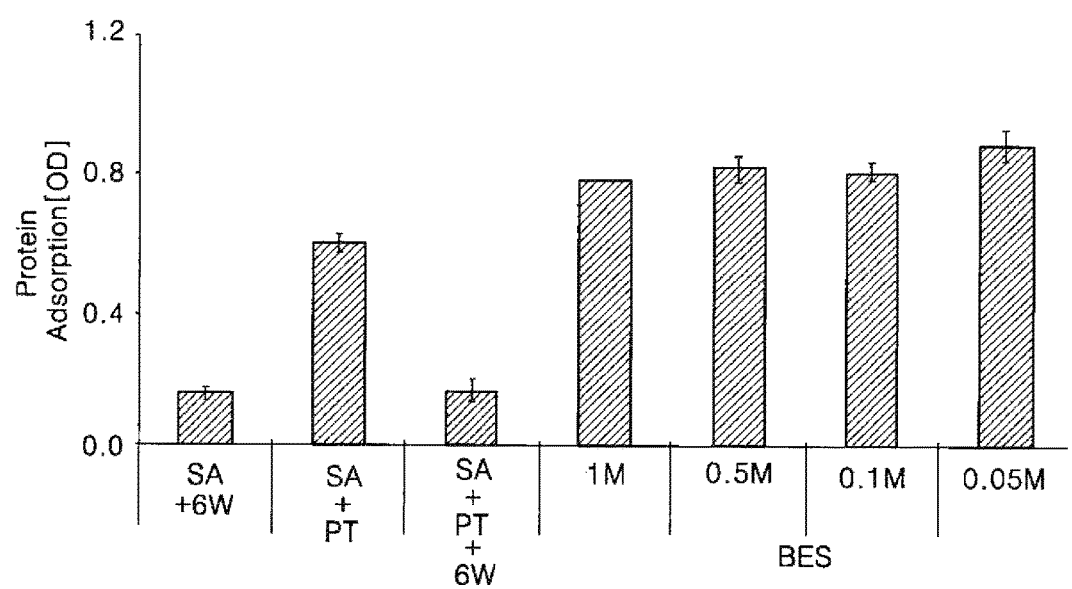
FIG. 8 shows the measurement results of the blood-protein adhering amount of the dental implant after preparing the mixed solution depending on the concentration of BES being the organic amphiphilic substance having sulfonic group and the pH buffering agent, and coating and accelerating it.
Figure 9:
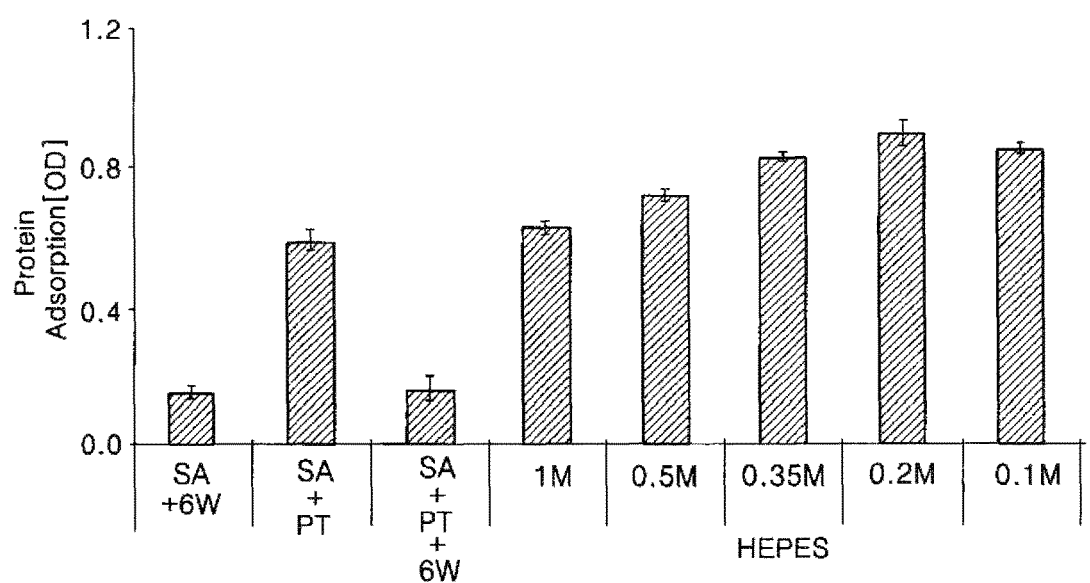
FIG. 9 shows the measurement results of the blood-protein adhering amount of the dental implant after preparing the mixed solution depending on the concentration of HEPS being the organic amphiphilic substance having sulfonic group and the pH buffering agent, and coating and accelerating it.
Figure 10:
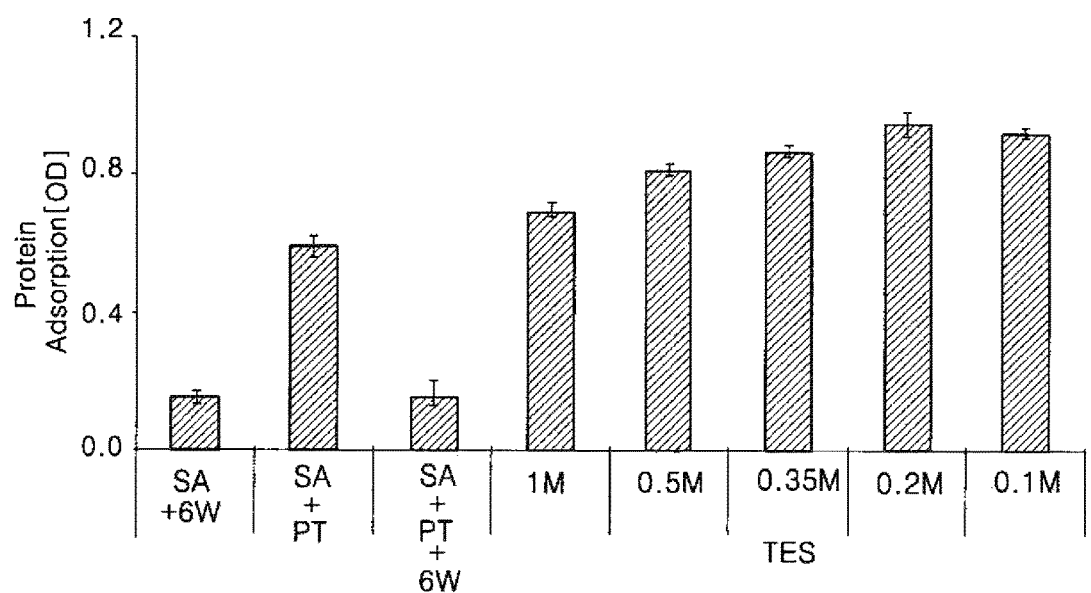
FIG. 10 shows the measurement results of the blood-protein adhering amount of the dental implant after preparing the mixed solution depending on the concentration of TES being the organic amphiphilic substance having sulfonic group and the pH buffering agent, and coating and accelerating it.

As can be confirmed from the results of FIGS. 8~10, it could be confirmed that despite the acceleration aging for 6 weeks, it could be ascertained that the implant on which the mixed solution of the pH buffering agent and the organic amphiphilic substance having sulfonic group (BES, HEPES, TES) is coated has an excellent adhering capability of the blood-protein in all of the concentrations of 0.05~0.5M, and in particular it could be observed that the adhering capability of the blood-protein was remarkably increased in the case that said organic amphiphilic substance has the concentration range of 0.1~0.5M.

The present invention is not limited to a certain example and description as described above, and those having ordinary knowledge in the art to which the present invention belongs can practice various modification practices without departing from the spirit of the present invention as claimed in the claims, and those modifications are within the technical scope of the present invention.

The present invention has the effects preventing that the dental implant is exposed to air before it is inserted into the alveolar bone and the implant surface is re-contaminated; improving the biocompatibility of the implant, fluid- and blood-affinity, and the initial osseointegration performance by avoiding the bioactivity due to the surface-hydrophobicizing, and effectively avoiding the adsorption of the contaminant in the air and also increasing the initial osseointegration performance after the implant surgery because of the coating layer uniformly formed on the surface, representing the biocompatibility and fluid- and blood-affinity; and finally shortening the osseointegration period, and therefore, the present invention has the industrial applicability.

The invention claimed is:

1. A bioactive hydrophilic dental implant which is made of titanium or titanium alloy and has a rough surface,
wherein a coating layer of a mixed solution comprising i) an organic pH buffering agent and an inorganic pH buffering agent and ii) an organic amphiphilic substance having a sulfonic group is formed on the rough surface which was subject to pre-treatment for removal of a contaminant,
wherein the organic pH buffering agent has a pKa of 8.0 or more and comprises at least one of AMPD, ammonia, bicine, glycine, glycylglycine, tris, tricine and taurine,
wherein the inorganic pH buffering agent has a hydroxyl group and comprises at least one of NaOH, KOH, Ca(OH)$_2$, Ba(OH)$_2$, Al(OH)$_3$ and Sr(OH)$_2$,
wherein the organic amphiphilic substance having the sulfonic group comprises at least one of ACE, BES, CHES, HEPES, MOPS, PIPES and TES, and
wherein in the mixed solution, the organic amphiphilic substance having the sulfonic group has a concentration of 0.05~1.68M, and the organic pH buffering agent and the inorganic pH buffering agent is used in a range of 1-10 wt % of the mixed solution.

2. A method for preparing a bioactive hydrophilic dental implant, the method comprising:
preparing dental implant made of titanium or titanium alloy;
roughening a surface of the dental implant;
removing a contaminant from the roughened surface by pre-treating the roughened surface of the dental implant; and
forming, on the roughened surface from which the contaminant is removed, a coating layer of a mixed solution comprising i) an organic pH buffering agent and an inorganic pH buffering agent and ii) an organic amphiphilic substance having a sulfonic group,
wherein the organic pH buffering agent has a pKa of 8.0 or more and comprises at least one of AMPD, ammonia, bicine, glycine, glycylglycine, tris, tricine and taurine,
wherein the inorganic pH buffering agent has a hydroxyl group and comprises at least one of NaOH, KOH, Ca(OH)$_2$, Ba(OH)$_2$, Al(OH)$_3$ and Sr(OH)$_2$,
wherein the organic amphiphilic substance having the sulfonic group comprises at least one of ACE, BES, CHES, HEPES, MOPS, PIPES and TES, and
wherein in the mixed solution, the organic amphiphilic substance having the sulfonic group has a concentration of 0.05-1.68M, and the organic pH buffering agent and the inorganic pH buffering agent is used in a range of 1-10 wt % of the mixed solution.

3. The method according to claim 2, wherein the removing of the contaminant comprises treating the roughened surface of the dental implant with at least one of ultraviolet ray, radio-frequency glow discharge (RFGD), and oxygen and room temperature plasma.

\* \* \* \* \*